United States Patent [19]

Brett et al.

[11] Patent Number: 5,041,279

[45] Date of Patent: Aug. 20, 1991

[54] DENTAL CREAM PACKAGE

[75] Inventors: Marie Brett, Hazel Grove; Harry Hayes, Warrington, both of England

[73] Assignee: Colgate-Palmolive Company, Piscataway, N.J.

[21] Appl. No.: 496,724

[22] Filed: Mar. 21, 1990

Related U.S. Application Data

[63] Continuation of Ser. No. 214,786, Jul. 5, 1988, abandoned, which is a continuation of Ser. No. 835,014, Feb. 28, 1986, abandoned.

[51] Int. Cl.$^5$ .............................. A61K 7/16; A61K 7/8
[52] U.S. Cl. ........................................ 424/52; 424/49
[58] Field of Search ..................................... 424/49, 52

[56] References Cited

U.S. PATENT DOCUMENTS

| | | | |
|---|---|---|---|
| 3,260,410 | 7/1977 | Drandt et al. | 222/107 |
| 3,662,060 | 5/1972 | Clippingdale et al. | 424/57 |
| 3,957,968 | 5/1976 | Cordon | 424/57 |
| 4,418,841 | 12/1983 | Eckstein | 222/107 |
| 4,437,591 | 3/1984 | von Schuckmann | 222/405 |
| 4,556,553 | 12/1985 | Suganuma | 424/52 |

OTHER PUBLICATIONS

Lion Corp., JP-184116, Abstract, Apr. 27, 1985, Derwent Abst. No. C85-060489, Dentifrice Compsn. Charged in Water-Permeable Plastic Container Contains a Glycerine-Contg. Humactant.

*Primary Examiner*—F. T. Moezie
*Attorney, Agent, or Firm*—Robert L. Stone; Murray M. Grill

[57] ABSTRACT

Dental cream in contact with a polyolefin resin surface of a package such as a laminate tube, a mechanical dispenser or a flexible sachet. The dental cream contains at least a major amount of dentally acceptable water-insoluble polishing material, alpha-alumina trihydrate, a liquid aqueous humectant vehicle wherein glycerine and sorbitol are humectants, a gelling agent and benzoic acid to reduce pH and prevent syneresis due to contact between the dental cream and the polyolefin resin.

11 Claims, No Drawings

DENTAL CREAM PACKAGE

This is a continuation of application Ser. No. 07/214,786 filed 7/5/88; which is a continuation of Ser. No. 06/835,014 filed 2/28/86, both are now abandoned.

This invention relates to a dental cream packaged in a plastic laminate tube, mechanical dispenser, flexible sachet or the like. In particular it relates to a dental cream in compatible contact with a polyolefin surface of a package such as a plastic laminate dental cream tube, mechanical dispenser or flexible sachet.

Dental creams have been packaged for many years in flexible metal tubes such as wax lined lead tubes, unlined aluminum tubes or aluminum tubes having an epoxy resin lacquer coating thereon. In recent years flexible form-retaining laminated plastic tubes have been increasingly used.

Plastic laminated dental cream tubes typically comprise an inner polyolefin resin layer which is in direct contact with the dental cream and at least one intermediate layer, including an aluminum foil layer which inhibits loss of flavor from the dental cream. Desirably, an intermediate paper layer which provides stiffness to the tube is also present. The outer layers are typically of polyolefin resins, one of which may be colored white and bears printed indicia with a clear polyolefin laminate overlay to protect the indicia. Additional intermediate laminate layers of flexible plastic may also be present.

Mechanical dental cream dispensers may also have a polyolefin surface in contact with dental cream contained therein. In fact, the polyolefin itself may be the housing of the dispenser. Flexible sachet packets may also have a polyolefin surface in contact with dental areas.

Dental creams typically contain a liquid vehicle of water and humectant, a gelling agent solid vehicle and a water-soluble dental polishing agent. Dental creams composed of such materials wherein the humectant comprises glycerine and sorbitol and the polishing material is at least in major part an alpha alumina trihydrate have been successfully packaged in flexible metal toothpaste containers including aluminum tubes having an internal coating of an epoxy resin lacquer layer. However, it has been observed that when such dental creams are packaged in containers having an interior polyolefin surface such as plastic laminated dental cream tubes, mechanically operated dental cream dispensers or flexible sachets, that syneresis occurs and liquids separate from solids, rendering the dental cream undesirable, when the pH of the dental cream is reduced with a water-soluble material which provides phosphate ion. In commonly assigned U.S. patent application for "Packaged Dental Cream" filed Nov. 27, 1985 of Sandra Lee Schelm, syneresis of such a dental cream in contact with polyolefin surface is overcome by including polyethylene glycol of average molecular weight of about 200–1000 in the dental cream.

It is an advantage of this invention that phase separation of a dental cream packaged in contact with a polyolefin material is substantially prevented with an acidifying agent. Other advantages will be apparent from consideration of the following disclosure.

In accordance with certain of its aspects, this invention relates to a dental cream package wherein said dental cream is in direct contact with a polyolefin resin surface, said dental cream comprising at least about 25% by weight of a liquid vehicle comprising water, glycerine and sorbitol, the weight ratio of glycerin to sorbitol being from 0.25:1 to about 3:1, a solid vehicle comprising about 0.05%–10% by weight of gelling agent, about 20–75% by weight of a dentally acceptable water-insoluble polishing material, at least a major portion of which is alpha-alumina trihydrate and benzoic acid to reduce the pH of the dental cream to about 6–8.5.

In dental cream formulations, the liquids and solids are necessarily proportioned to form a creamy mass of desired consistency which is extrudible from its package. The liquids in the present dental cream comprise chiefly water, glycerine and sorbitol. The total liquid vehicle comprises at least about 20% by weight of the formulation. It is preferred to use also a gelling agent in dental creams such as the natural and synthetic gums and gumlike materials, e.g. carrageenans such as Irish moss, gum tragacanth, sodium carboxymethyl cellulose, hydroxyethyl cellulose, polyvinyl pyrrolidone, sodium alginate, guar gum, starch, xanthan and the like, including mixtures thereof. Irish Moss, sodium carboxymethyl cellulose and hydroxyethyl cellulose including mixtures thereof are compatible particularly and are preferred gelling agents. The gum content is usually in an amount about 0.05–10% and preferably about 0.5–5% by weight of the formulation.

Water is generally incorporated into the dental cream in amount of about 10–50% by weight, preferably about 15–35%. Glycerine and sorbitol together generally comprise about 15–50% by weight, preferably about 20–35% of the dental cream, with the weight ratio of glycerine to sorbitol being from about 0.25:1 to about 3:1, typically from about 0.25:1 to about 0.8:1 and preferably from 0.6:1 to about 0.8:1. Amounts of sorbitol as used herein are of sorbitol syrup, as commercially available, that is 70% by weight sorbitol in 30% by weight of water.

Dentally acceptable water-insoluble polishing agent is present in the dental cream in amount of about 20–75% by weight, preferably about 35–60%. At least the major portion, that is, about 50–100% of the polishing material is alpha-alumina trihydrate. The minor portion of the polishing material, if present, typically comprises about 5–20% by weight of the polishing material. Dicalcium, phosphate dihydrate, anhydrous dicalcium phosphate, calcium carbonate, tricalcium phosphate, calcium pyrophosphate, dimagnesium phosphate trihydrate, magnesium carbonate, calcined alumina, zirconium silicate and insoluble sodium metaphosphate are typical.

Dentally acceptable water-insoluble alpha-alumina toothpaste is typically employed in small particle size, e.g. wherein at least about 85% of the particles are smaller than 20 microns and is preferably hydrated, such as that classified as gibbsite (alpha alumina trihydrate) and normally represented chemically as $Al_2O_3 \cdot 3H_2O$ or $Al(OH)_3$. The average particle size of gibbsite is generally about 6 to 9 microns. However, larger particle size alpha-alumina trihydrate, e.g. wherein 20–70% of the particles exceed 20 microns in size, may also be used. A particularly desirable grade of alpha-alumina trihydrate, available from Alcoa as C-333 is a fine grade of gibbsite having the following size distribution:

| Microns | Percent |
| --- | --- |
| <30 | 94–99 |

| Microns | Percent |
| --- | --- |
| <20 | 85-93 |
| <10 | 56-67 |
| <5 | 28-40 |

Other desirable grades of alpha-alumina trihydrate include BACO AF-230 and BACO AF-260, available from British Alcoa Aluminium, SH100 from Rhone Poulenc, and OS4608 and ON4608 grades from Martinswerk.

Unless the pH of the dental cream is adjusted, dental cream containing a substantial amount of alpha-alumina trihydrate is generally highly alkaline, e.g. about 9-10.5. Accordingly acidic materials are often added to such dental creams in order to reduce the pH, typically to about 6 to 8.5. As set forth above, when water-soluble phosphate materials are employed to produce such reduction in alkalinity, syneresis occurs unless a further additive, polyethylene glycol of average molecular weight of about 200-1000, is present. In the present Specification reference to the pH is as measured in a 20% aqueous slurry.

In the present invention it has been found that when the pH is adjusted to about 6-8.5 with benzoic acid syneresis in the presence of a polyolefin package surface is prevented. Typically about 0.15-0.5% by weight of benzoic acid is effective to produce a pH of about 6-8.5 with various grades of alpha-alumina trihydrate in dental cream. It is preferred that the pH of the dental cream be about 7.5-8.5. Reference to pH herein is to a 20% by weight aqueous slurry of dental cream.

Organic surface-active agents may be used in the dental cream of the present invention to achieve increased prophylactic action, assist in achieving thorough and complete dispersion of the instant compositions throughout the oral cavity and render the dental creams more cosmetically acceptable. The organic surface-active material may be anionic, nonionic, ampholytic or cationic in nature, but it is preferred to employ as the surface-active agent a detersive material which imparts to the composition detersive and foaming properties. Suitable types of such detergents are water-soluble salts of higher fatty acid monoglyceride monosulphates, such as the sodium salt of the monosulphated monoglyceride of hydrogenated coconut oil fatty acids, higher alkyl sulphates, such as sodium lauryl sulphate, alkylaryl sulphonates, such as sodium dodecyl benzene sulphonate, olefinsulphonates, such as sodium olefin sulphonate in which the olefin group contains 12-22 carbon atoms, higher alkyl sulphoacetates, higher fatty acid ester of 1,2-dihydroxy propane sulphonates, and the substantially saturated higher aliphatic acyl amides of lower aliphatic amino carboxylic acid compounds such as those having 12-16 carbon atoms in the fatty acid, alkyl or acyl radicals and the like. Examples of the last mendoned amides are N-lauroyl sarcosine, and the sodium, potassium, and ethanolamine salts of N-lauroyl, N -myristoyl or N-palmitoyl sarcosine, which should be substantially free from soap or similar higher fatty acid material which tends to substantially reduce the effect of these compounds in compositions of the present invention. The amides are particularly advantageous since they exhibit a prolonged and marked effect in the inhibition of acid formulation in the oral cavity due to carbohydrates breakdown in addition to exerting some reduction in the solubility of tooth enamel in acid solutions. Another desirable material is a long chain fatty acid sodium monoglyceride sulphonate used alone or in combination with sodium lauryl sulphate.

Other particularly suitable surface-active materials include nonionic agents such as condensates of sorbitan monostearate with approximately 20 moles of ethylene oxide, condensate of ethylene oxide with propylene glycol ("Pluronic" materials) and amphoteric agents such as long chain (alkyl) amino-alkylene alkylated amine derivatives, which are available under the trademark "Miranol" such as Miranol $C_2M$. Cationic surface-active germicides and antibacterial compounds such as di-isobutyl phenoxy ethoxy ethyl dimethyl benzyl ammonium chloride, benzyl dimethyl stearyl ammonium chloride, benzyl diethyl stearyl ammonium chloride, tertiary amines having one fatty alkyl group (of from 12-18 carbon atoms) and two (poly) oxyethylene groups attached to the nitrogen (typically containing a total of from about 2 to 50 ethanoxy groups per molecule) and salts thereof with acids, and compounds of the structure

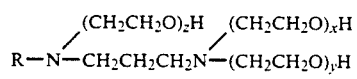

where R is a fatty alkyl group containing from about 12 to 18 carbon atoms, and x, y and z total 3 or higher, as well as salts thereof with mineral or organic acids, may also be used. It is preferred to use from about 0.05 to 5% by weight of the foregoing surface-active materials in the dental cream. It is most preferred that the surface-active agent be an anionic material, particularly sodium lauryl sulphate.

The dental cream suitably may also contain a fluorine-containing compound having a beneficial effect on the care and hygiene of the oral cavity, e.g., diminution of enamel solubility in acid and protection of the teeth against decay. Examples thereof include sodium fluoride, stannous fluoride, potassium fluoride, potassium stannous fluoride ($SnF_2.KF$), sodium hexafluorostannate, stannous chlorofluoride, sodium fluorozirconate, and sodium monofluorophosphate. These materials which disassociate or release fluorine-containing ions in water, suitably may be present in an effective but non-toxic amount, usually within the range of about 0.01 to 1% by weight of the water soluble fluorine content thereof.

The preferred fluorine-containing compound is sodium monofluorophosphate typically present in an amount of about 0.076 to 7.6% by weight, preferably 0.76%. A mixture of sodium monofluorophosphate and sodium fluoride is also desirable, for instance in a weight ratio of about 2:1 or 1:1 based on fluoride, in amounts preferably providing about 1500-1450 ppm soluble fluoride.

Any suitable flavoring or sweetening materials may be employed in formulating a flavor for the composition of the present invention. Examples of suitable flavoring constituents include the flavoring oils, e.g., oils of spearmint, peppermint, wintergreen, sassafras, clove, sage, eucalyptus, marjoram, cinnamon, lemon and orange, as well as methyl salicylate. Suitable sweetening agents include sucrose, lactose, maltose, xylitol, sodium 6-methyl-3,4-dihydro-1,2,3-oxathiazine-4-one, sodium cyclamate, perillartine and sodium saccharin. Suitably, flavor and sweetening agents may together comprise from about 0.01 to 5% or more of the compositions of the instant invention.

Various other materials may be incorporated in the dental cream. Examples thereof are coloring or whitening agents or dyestuffs. anti-corrosive agents, preservatives, silicones, chlorophylic compounds, ammoniated materials such as urea, diammonium phosphate and mixtures thereof and other constituents. Whitening agents, such as titanium dioxide, typically in amounts of about 0.5-2%, may be beneficial to the appearance of the dental composition, since upon aging, some discoloration may occur. It is noteworthy that sodium benzoate preservative may assist in reducing syneresis of the dental cream in contact with polyolefin surface, typically when present in amount of about 0.25-0.75% by weight; preferably about 0.5%.

The adjuvants are incorporated in the instant compositions in amounts which do not substantially adversely affect the properties and characteristics desired and are selected and used in proper amounts depending upon the particular type of composition involved.

Antibacterial agents may also be employed in the oral compositions of the instant invention in an amount of about 0.01-5% by weight. Typical antibacterial agents include:

$N^1$-(4-chlorobenzyl)-$N^5$-(2,4-dichlorobenzyl) biguanide;
p-chlorophenyl biguanide;
4-chlorobenzhydryl biguanide;
4-chlorobenzhydrylguanylurea;
N-3-lauroxypropyl-$N^5$-chlorobenzylbiguanide;
1,6-di-chlorophenylbiguanidohexane;
1,6-bis-(2-ethylhexylbiguanide) hexane;
1-(lauryldimethylammonium)-8-(p-chlorobenzyldimethylammonium) octane dichloride;
5,6-dichloro-2-guanidinobenzimidazole;
$N^1$-p-chlorophenyl-N5-laurylbiguanide;
5-amino-1,3-bis(2-ethylhexyl)-5-methylhexahydropyrimidine and their non-toxic acid additon salts.

The package into which the dental cream is incorporated may be any polyolefin laminate dental cream tube. For instance, the tube may be as elementary as is described in U.S. Pat. No. 3,260,410 to Brandt et al, the disclosure of which is incorporated herein by reference. As described in the example thereof, an aluminum foil base having a thickness of about 0.0013 cm was heated to a temperature of approximately 177° C., and one face of the heated foil was contacted by an extrudable film of a random copolymer of ethylene and acrylic acid (acid content 3±0.5% and melt index 8±1), while the opposite surface thereof had placed thereagainst a film of low density polyethylene.

Using driven rolls a laminated base was obtained in which the copolymer layer was about 6 mils and the polyethylene layer was approximately 5 mils in thickness. The base was then shaped into tubular form and sealed.

After severing the tubular form into tube bodies, the tubes can be packed with the dental cream of the present invention Polyolefin laminate dentifrice tubes containing more intermediate layers may also be successfully used with the dental cream of the present invention without undergoing syneresis. For instance, the multiple layer flexible sheet structure for dental cream tubes described as "Prior Art" in U.S. Pat. No. 4,418,841 to Eckstein may be employed as well as the more crack resistant structures described therein. The disclosure of U.S. Pat No. 4,418,841 to Eckstein is incorporated herein by reference. In fact, dental creams of the present invention packed in tubes of sheet material identified as Prior Art A and A-1 in U.S. Pat. No. 4,418,841 are very satisfactory and undergo substantially no syneresis. Such tubes A and A-1 are comprised of layers as set forth below, in the order of outermostlayer to innermost layer.

| A | A-1 |
|---|---|
| 1.5 mil LDPE | 1.5 mil LDPE |
| 2.0 mil Pigmented LDPE | 2.0 mil Pigmented LDPE |
| 1.6 mil Paper | 1.6 mil Paper |
| 0.7 mil LDPE | 2.0 mil LDPE |
| 3.3 mil EAA | 1.0 mil OPP |
| 0.7 mil Foil | 1.0 mil EAA |
| 2.0 mil EAA | 0.7 mil Foil |
| 1.2 mil LDPE | 2.0 mil EAA |
| 13.0 mil Total | 1.2 mil LDPE |
| | 13.0 mil Total |

In A and A-1 the abbreviations have the following meanings:

| LDPE | low density polyethylene |
|---|---|
| EAA | ethylene acrylic acid |
| OPP | oriented polypropylene |

Mechanically operated dispensers, such as the dispenser for, in particular, pasty substances, described in U.S. Pat. No. 4,437,591 to von Schuckmann, the disclosure of which is incorporated herein by reference, may also be used with the practice of the present invention. The housing of such dispensers is commonly composed of a polyolefin resin such as polypropylene. Thus the housing resin is in essence a layer, the inner surface of which is in contact with dental cream. When the dental cream of the present invention is packaged in such a polypropylene mechanical dispenser, it undergoes substantially no syneresis.

The advantages of the invention are also present when the dental cream is packed in a flexible sachet having a polyolefin surface, typically of low density or medium density polyethylene.

The following illustrative examples are further illustrative of the nature of the present invention but it is understood that the invention is not limited thereto. All amounts and proportions are by weight except as otherwise indicated.

EXAMPLE I

The following dental creams are prepared to creamy consistencies and packed into tubes of each of laminated structures A and A-1, set forth above:

| | Parts | |
|---|---|---|
| | A | B |
| Glycerine | 10.000 | 10.000 |
| Sorbitol (70%) | 17.000 | 17.000 |
| Sodium Carboxymethyl cellulose | 0.900 | 0.900 |
| Sodium Saccharin | 0.200 | 0.200 |
| Tetrasodium pyrophosphate | 0.250 | 0.250 |
| Sodium Monofluorophosphate | 0.760 | 0.760 |
| Sodium Fluoride | 0.100 | 0.100 |
| Benzoic acid | 0.250 | 0.250 |
| Sodium Benzoate | 0.500 | — |
| Deionized water-irradiated | 15.646 | 16.146 |

-continued

|  | Parts | |
| --- | --- | --- |
|  | A | B |
| Alpha-alumina trihydrate (BACO AF-230) | 51.500 | 51.500 |
| Titanium Dioxide | 0.500 | 0.500 |
| Sodium lauryl sulfate (90%) | 1.444 | 1.444 |
| Flavor | 0.950 | 0.950 |
| pH (20% slurry) | 8.2 | 8.2 |

After aging for at least 9 weeks at 49° C., dental creams (1) and (2) remain creamy in consistency in laminate tubes of each of laminate Structures A and A-1. Similarly formulated dental creams with sodium diacid orthophosphate to reduce the pH quickly separate at room temperature and 49° C. in both of tubes of Structures A and A-1.

EXAMPLE 2

Dental creams (1) and (2) are incorporated into a mechanical dispenser in accordance with U.S. Pat. No. 4,437,591 coposed of polypropylene housing. Dental creams (1) and (2) retain their creamy consistency.

EXAMPLE 3

Similar results to those described above for Examples 1 and 2 are observed when:
(i) the relative amounts of glycerine and sorbitol (70%) are 6:24 and 18:6;
(ii) Sodium fluoride is omitted and its amount replaced by water;
(iii) The dental creams are packed in laminated tubes in accordance with U.S. Pat. No. 3,260,410;
(iv) The dental creams are packed in crack-resistant laminated tubes in accordance with U.S. Pat. No. 4,418,841;
(v) The dental creams are packed in flexible sachets of the following structure from outermost to innermost layer:
12.2μ polyethylene terephthalate
21.3μ white ethylene acrylic acid
9.0μ foil
3.3μ ethylene acrylic acid
25.4μ medium density polyethylene;
(vi) BACO AF-230 alpha-alumina trihydrate is replaced by each of Alcoa C-333, Rhone Poulenc SH100, Martinswerk OS4608 and ON4608 alpha-alumina trihydrate;
(vii) 3.000 parts of calcined alumina replace 3.000 parts of alpha-alumina trihydrate; and
(viii) 10 parts of insoluble sodium metaphosphate replace 10.000 parts of alpha-alumina trihydrate.
(ix) sodium cyclamate replaces sodium saccharin.

It is understood that the foregoing detailed description is given merely by way of illustration and that variations may be made therein without department from the spirit of the invention.

What is claimed:

1. A dental cream package wherein said dental cream is in direct contact with a low or medium density polyethylene or polypropylene surface;
   wherein said dental cream comprises a solid vehicle and an aqueous vehicle; wherein said aqueous vehicle comprises:
   (a) water, present in a quantity of from about 10 to about 50% by weight of the dental cream and
   (b) glycerine and sorbitol, together present in a quantity of from about 15 to about 50% by weight of the dental cream, the weight ratio of said glycerine to said sorbitol ranging from about 0.25:1 to about 3:1;
   wherein said solid vehicle comprises:
   (a) a dental cream gelling agent present in a quantity of from about 0.05 to about 10% by weight of said dental cream,
   (b) a dentally acceptable water-insoluble polishing material of which at least 50% by weight is alpha-alumina trihydrate having a pH of from about 9 to about 10.5, said trihydrate having a pH of from about 9 to about 10.5, said polishing material being present in a quantity of from about 20 to about 75% by weight of said dental cream; and
   wherein said dental cream in the absence of benzoic acid and in contact with said polyethylene or polypropylene surfaces, exhibits syneresis; said dental cream further comprising a syneresis inhibiting effective quantity of benzoic acid in an amount to reduce the pH of the dental cream to about 6 to about 8.5.

2. The dental cream package of claim 1 wherein the weight ratio of glycerine to sorbitol is from about 0.25:1 to about 0.8:1.

3. The dental cream package of claim 2 wherein the weight ratio of glycerine to sorbitol is from about 0.6:1 to about 0.8:1.

4. The dental cream package of claim 1 wherein benzoic acid is present in amount of about 0.15-0.5%.

5. The dental cream package of claim 1 wherein about 0.25-0.75% by weight of sodium benzoate is present.

6. The dental cream package of claim 1 wherein flouride providing compound is also present in an amount, based on the water soluble flouride content, of from about 0.01 to about 1% by weight of the dental cream.

7. The dental cream package of claim 6 wherein said compound is sodium monofluorophosphate.

8. The dental cream package of claim 6 wherein said compound is a mixture of sodium monofluorophosphate and sodium flouride.

9. The dental cream of claim 1 packaged in a plastic laminated tube.

10. The dental cream package of claim 1 wherein said dental cream is packaged in a mechanical dispenser having a housing of polyolefin resin.

11. A dental cream package wherein
said dental cream is in direct contact with a low or medium density polyethylene or polypropylene surface;
wherein said dental cream comprises a solid vehicle and an aqueous vehicle;
wherein said aqueous vehicle comprises:
   (a) water, present in a quantity of from about 10 to about 50% by weight of the dental cream and
   (b) glycerine and sorbitol, together present in a quantity of from about 15 to about 50% by weight of the dental cream, the weight ratio of said glycerine to said sorbitol ranging from about 0.25:1 to about 3:1;
wherein said solid vehicle comprises:
   (a) a dental cream gelling agent present in a quantity of from about 0.05 to about 10% by weight of said dental cream,
   (b) a dentally acceptable water-insoluble polishing material of which at least 50% by weight is alpha-alumina trihydrate having a pH of from about 9 to about 10.5, said trihydrate having a pH of from about 9 to about 10.5, said polishing material being present in a quantity of from about 20 to about 75% by weight of said dental cream; and wherein said dental cream, in the absence of benzoic acid and in contact with said polyethylene or polypropylene surfaces, exhibits syneresis; said dental cream further comprising a syneresis inhibiting effective quantity of benzoic acid in an amount to reduce the pH of the dental cream to about 7.5 to about 8.5.

* * * * *